United States Patent [19]

Vernon et al.

[11] Patent Number: 4,924,182
[45] Date of Patent: May 8, 1990

[54] EDDY CURRENT METHOD TO MEASURE DISTANCE BETWEEN SCANNED SURFACE AND A SUBSURFACE DEFECT

[75] Inventors: Susan N. Vernon, Annandale, Va.; Paul M. Gammell, Silver Spring, Md.

[73] Assignee: The United States of America as represented by the Secretary of the Navy, Washington, D.C.

[21] Appl. No.: 294,621

[22] Filed: Jan. 9, 1989

[51] Int. Cl.$^5$ .................... G01N 27/87; G01N 27/90
[52] U.S. Cl. .................... 324/237; 324/233; 324/232; 324/225
[58] Field of Search ............ 324/209, 228, 227, 226, 324/225, 232–243, 260, 262

[56] References Cited

U.S. PATENT DOCUMENTS

| | | | |
|---|---|---|---|
| 3,449,664 | 6/1969 | Smith | 324/235 |
| 4,006,407 | 2/1977 | Flaherty et al. | 324/233 |
| 4,041,379 | 8/1977 | Karlsson | 324/260 |
| 4,107,605 | 8/1978 | Hudgell | 324/220 |
| 4,337,431 | 6/1982 | Hale | 324/220 |
| 4,355,281 | 10/1982 | Toth et al. | 324/237 X |
| 4,413,231 | 11/1983 | Amedro et al. | 324/220 |
| 4,467,281 | 8/1984 | Davis et al. | 324/237 X |
| 4,495,587 | 1/1985 | Plante et al. | 324/237 X |
| 4,496,904 | 1/1985 | Harrison | 324/227 |
| 4,507,608 | 3/1985 | Flach et al. | 324/237 X |
| 4,667,149 | 5/1987 | Cohen et al. | 324/64 |
| 4,719,422 | 1/1988 | deWalle et al. | 324/238 |
| 4,739,261 | 4/1988 | Sugiyama et al. | 324/232 |
| 4,745,809 | 5/1988 | Collins et al. | 73/661 |
| 4,747,310 | 5/1988 | Collins et al. | 73/661 |
| 4,761,610 | 8/1988 | Svegander et al. | 324/237 X |
| 4,763,071 | 8/1988 | McGee et al. | 324/236 X |
| 4,821,204 | 4/1989 | Hüschelvath | 324/237 X |
| 4,823,082 | 4/1989 | Nasu et al. | 324/225 X |

FOREIGN PATENT DOCUMENTS

| | | | |
|---|---|---|---|
| 86/01896 | 3/1986 | World Int. Prop. O. | 324/238 |
| 86/02456 | 4/1986 | World Int. Prop. O. | 324/237 |

Primary Examiner—Reinhard J. Eisenzopf
Assistant Examiner—Warren S. Edmonds
Attorney, Agent, or Firm—John D. Lewis; Kenneth E. Walden

[57] ABSTRACT

This invention relates to a method for nondestructive inspection (NDI) of composite materials comprising conductive fibers. The depth of broken fiber damage in nonmetal matrix composites such as graphite/epoxy and carbon/carbon materials may be ascertained and eddy current inspection is extended to include thick metal sections by this method. Inspection is possible with access limited to a single surface.

45 Claims, 3 Drawing Sheets

EDDY CURRENT METHOD TO MEASURE DISTANCE BETWEEN SCANNED SURFACE AND A SUBSURFACE DEFECT

The invention described herein may be manufactured and used by or for the Government of the United States of America for governmental purposes without the payment of any royalties thereon or therefor.

The present invention relates to the field of nondestructive inspection of materials. In particular, a method of eddy current inspection for estimating the distance between the scanned surface and a subsurface defect of unknown geometry in electrically conductive materials is disclosed. This method is particularly useful in measuring the depth of broken fiber damage such as may result from impact damage in carbon fiber reinforced composites having nonmetallic matrices.

BACKGROUND OF THE INVENTION

With the increased use of graphite epoxy, particularly in aerospace, there is an increasing demand for a field-applicable, nondestructive method to detect and to measure the severity of service-incurred damage in this material. Ideally, a field applicable system is safe, portable, provides manual or rapid automated scanning, and allows real time interpretation. The method also must provide for single-sided inspection since frequently only one surface is accessible.

Impact is a common source of service-incurred damage in graphite epoxy components and, unfortunately, there is no such thing as "typical" impact damage. Impact damage may consist of varying densities of matrix cracking, delamination (separation of adjacent plies or lamina) and broken fibers. Low levels of impact cause delamination. Higher levels cause more extensive delamination and fiber breakage as well. There may be no visible damage on the impacted surface, yet subsurface damage may be extensive. The distribution of the damage depends on the thickness of the material and the extent to which it is supported as well as on the shape and consistency of the impactor and the force of the impact. In thin, unsupported panels the area of the damage tends to increase towards the back surface while the reverse may be true in thicker materials.

The effect of the damage depends on the type of stress to which the composite is subjected. Compressive strength is affected by delamination while fiber breakage has a greater effect on tensile strength. In both cases the residual strength depends on the amount of damage sustained; not only on the area of the damage measured in planes parallel to the surface but on the through-thickness extent of the damage as well.

The ultrasound pulse-echo A-scan method, known to those of ordinary skill in the materials inspection art, effectively detects delamination in graphite epoxy. Of the available technologies, this ultrasound method most closely meets the requirements for field-application, consequently it is the method that is currently used to inspect graphite epoxy for service incurred damage. Delamination can be detected by a manual scan using a contact transducer. The total area of the damaged region can also be imaged by a conventional C-Scan. The distance between the scanned surface and the delamination can be estimated from a pulse-echo A-Scan. Ultrasound field techniques have two generally recognized drawbacks: They require the use of a couplant material and, perhaps more important, the delamination nearest the scanned surface can mask delaminations that may be deeper in the material. The extent of deeper delamination has profound effects on the residual strength of the material.

In contrast, a properly optimized eddy current system, utilizing techniques described herein, is sensitive to the broken fibers associated with extensive delamination. The sensitivity of pulse-echo ultrasound under many circumstances is independent of the through-thickness extent of the damage. Eddy current is sensitive only to the broken fibers which tend to be associated with delamination extending through several plies. Combining the two methods thus provides an indication of the degree of severity of the damage detected by ultrasound. When the component is to be subjected only to tensile stress, or when only more severe delamination is of concern, Applicant's techniques will be the most efficacious inspection method available.

With the herein described method, eddy current can provide a measure of the thickness of the undamaged material between the surface and the subsurface broken fiber damage. This is analogous to the distance between the scanned surface and the nearest delamination provided by an ultrasonic A-Scan.

Currently available eddy current systems are oriented towards the inspection of surface defects on metal and for the through thickness inspection of thin metal foils or thin-walled tubing. Prior art techniques fail to address thicker metals or weakly conducting composites. By the proper selection of frequency and probe size, the disclosed method provides a capability to inspect these thicker metals and composites.

An example of the state of the art in materials testing is represented by Sugiyama, U.S. Pat. No. 4,739,261 filed April 19th, 1988 in which techniques are disclosed for inspecting ferromagnetic materials. In addition to the limitation of restricting the techniques to ferromagnetic materials, this reference does not address the problems inherent in testing thick materials and composites. In addition, standards in the form of calibration curves must be prepared in advance.

A related application by the same inventor filed Jan. 9, 1989, Ser. No. 294,622, entitled, Eddy Current Method for Measuring Electrical Resistivity and Device for Providing Accurate Phase Detection, discloses a method for measuring resistivity of carbon fiber reinforced composites and other weakly conducting materials.

The ability to measure the defect depth in a material has heretofore required calibration standards. These calibration standards require a test sample of material containing well characterized defects. The test material must be identical with the material to be inspected and the calibration defects must be representative of those expected to be located by the inspection. These standardization requirements severely limit the ability to quantify depth of damage in composites. With the spectrum of materials and defects growing ever larger, a need for an inspection method free of these calibration requirements is needed.

The inability to apply eddy current inspection techniques to thick metal components efficiently is generally recognized in the art. Methods disclosed herein provide this capability to materials thicker than those generally associated with eddy current techniques.

Therefore, it is an object of this invention to teach a method of nondestructive inspection of electrically conductive materials using eddy current techniques.

It is another object of the instant invention to disclose a method for nondestructive inspection that is efficacious when inspecting carbon fiber reinforced composites.

It is yet another object of the present invention to teach a method of nondestructive inspection that can estimate the distance between the scanned surface and a subsurface flaw to include internal broken fiber damage in a carbon fiber composite with a nonmetallic matrix.

It is still another object to disclose a method of nondestructive inspection that can estimate the distance between the scanned surface and subsurface flaws including matrix defects in metallic components.

It is a further object of the methods taught herein to provide the ability to nondestructively inspect metallic components for back surface breaking cracks or defects.

It is another object of the present invention to provide a method of nondestructive inspection of composites that can be performed with an appropriate probe and an assembly of off-the-shelf commercial electronics.

It is yet another object to provide a method of eddy current inspection of composites that can be performed with access restricted to a single surface of the material under test.

It is yet another object to teach a method of inspecting thick carbon fiber reinforced composite sections such as those developed for submersibles and space applications.

It is a further object to teach a method of inspecting carbon fiber reinforced composite sections such as those employed in the fabrication of pressure vessels.

It is yet another object to disclose a method of inpecting carbon fiber reinforced rocket nozzle components.

It is a further object to teach a method of eddy current inspection of materials free of the need for calibration standards.

It is another object to disclose an eddy current inspection method which utilizes the features of a ferrite cup-core probe.

Other objects, advantages and novel features of the invention will appear from a reading of the following detailed description of the invention when considered in conjunction with the accompanying drawings.

BRIEF DESCRIPTION OF THE DRAWINGS

FIG. 4 is an illustration of a ferrite cup core probe.

DETAILED DESCRIPTION OF THE INVENTION

Figure 1:
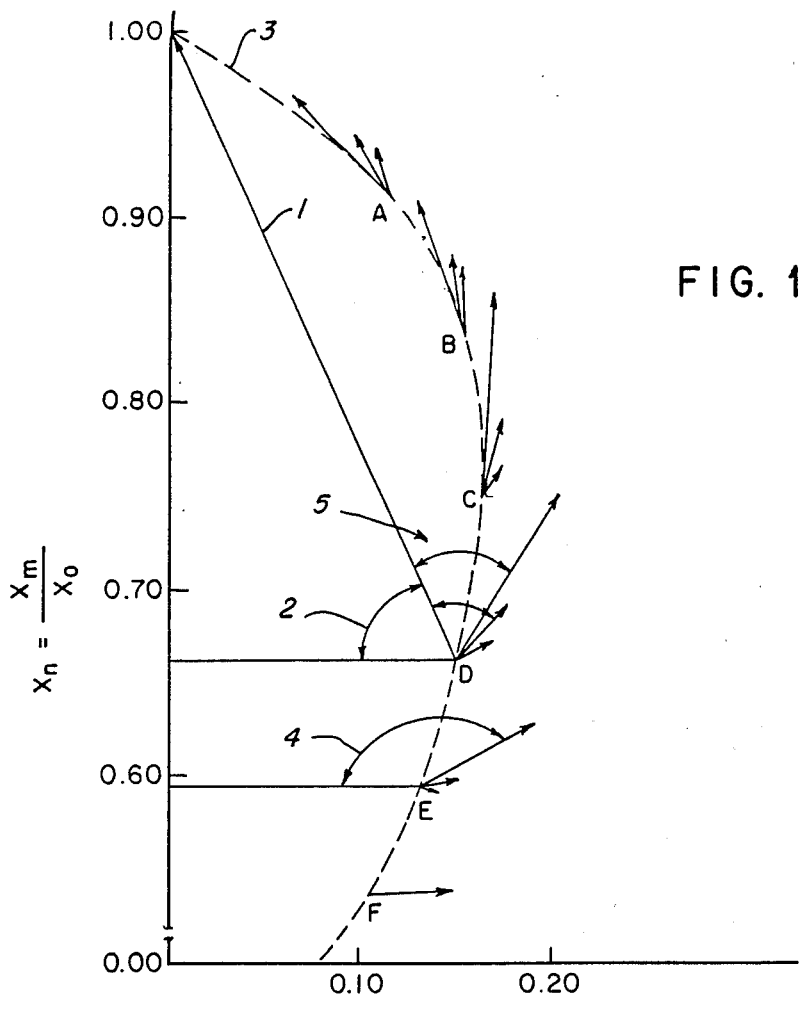
FIG. 1 is a normalized impedance diagram.

1. Discussion and examples.

The resistivity of carbon fiber reinforced composites (CFRC) is orders of magnitude higher than that of metals. The high resistivity offers both advantages and disadvantages. On the positive side, it permits inspection to greater depths than are generally associated with eddy current inspection. For example, the skin depth at 10 kHz in a material having a resistivity of 10,000 microhm.cm is 5 cm. On the other hand many components, such as aircraft wing skins, are much thinner than this and consequently require higher inspection frequencies than are usually required for the inspection of metals. For example, a skin depth of 5 mm in this same material would require an inspection frequency of 1 MHz. No commercial eddy current instruments were located that could provide accurate measurements at these higher frequencies, without modification. These methods are effective with any materials with a relative magnetic permeability of 1.

Applicants tested four eddy current instruments, each rated up to at least 1 MHz and two rated up to at least 6 MHz. With several commercial probes designed for use at the test frequencies, the difference in angle between the response to high resistivity carbon/carbon and the response to low resistivity aluminum was measured with a laboratory grade impedance analyzer and with each eddy current instrument. Results of tests of one of the eddy current instruments, typical of the results for all four tested, are given in Table 1. Listed are the rated frequency of each probe, the test frequency, the impedance of the probe in air at that frequency, the gain setting on the eddy current instrument and the difference in phase angle as measured by the eddy current instrument and by the impedance analyzer. In analyzing the data in Table 1 it should be remembered that angular separation depends on probe size as well as frequency.

TABLE 1

| RATED FREQ OF PROBE MHZ | TEST FREQ MHZ | PROBE IMPEDANCE IN AIR OHMS | E.C. INST. GN. SET NOMINAL | ANGLE DIFFERENCE | |
|---|---|---|---|---|---|
| | | | | ECI | IA |
| 2 | 1 | 28.3 | AO | −4° | 49° |
| | 2 | 64.3 | 20 | −14 | 43 |
| | 3 | 129.1 | 10 | 37 | 37 |
| 6 | 2 | 32.2 | 90 | −6 | 9 |
| | 3 | 52.6 | 90 | −3 | 8 |
| | 4 | 80.3 | 90 | −17 | 7 |
| 4 | 3 | 45.3 | 90 | −27 | 16 |
| | 4 | 66.3 | FF | 24 | 13 |
| | 5 | 144.3 | FF | 37 | 11 |

It is interesting to note that the eddy current instrument (ECI) and the impedance analyzer (IA) agreed only for the 2 MHz probe at 3 MHz which applicants interpret as coincidental since all other data indicate the eddy current measurement as highly inaccurate. Inaccuracies generally were noted on the order of plus or minus 10 to 20 degrees rendering the data unacceptable. Test results on the other eddy current instruments were similar as those presented in Table 1. Use of eddy current for the field inspection of graphite epoxy will require eddy current instruments to provide accurate high frequency phase detection.

Selection of the appropriate frequency requires knowledge of the material resistivity. If the entire thickness of the material is to be inspected then the frequency (lowest frequency in a multifrequency approach) must provide penetration of the electromagnetic field through the thickness of the material. If the frequency is much lower than necessary some defect sensitivity is lost.

The frequency selected is determined by the resistivity of the material and on its thickness, since, according to the skin depth relationship, in a nonmagnetic material, skin depth, in mm is given by $$S = 50.29(p/f)^{\frac{1}{2}}$$

where p is the resistivity in microhm.cm and f is the frequency in hertz. In the eddy current inspection of a set of metal components the resistivity generally can be assumed to be the same for all the components, to be independent of location on the component, and to be independent of frequency. These assumptions do not apply to graphite epoxy components. To ensure both penetration of the material and accurate interpretation of the data, resistivity measurements should be made over an appropriate frequency range as the component is scanned.

Selection of the appropriate frequency alone does not insure a defect detection and measurement capability. Equally important is the selection of probe size and type.

The importance of probe design parameters is witnessed by the normalized impedance diagram obtained by plotting the normalized imaginary ($X_n$) against the normalized real ($R_n$) components. These components are given by:

$$R_n = (R_b - R_o)/X_o \text{ and } X_n = X_b/X_o$$

where $R_b$ and $X_b$ are the real and imaginary components of the impedance when the probe is in contact with the test material and $R_o$ and $X_o$ are the corresponding values when the probe is in air.

Turning now to FIG. 1 wherein is shown the normalized impedance curve and defect response vectors generated with a 4.76 mm mean radius (r) ferrite cup core probe on carbon/carbon at frequencies and r/s values, respectively, of 125 kHz and 1.2 (A), 250 kHz and 1.6 (B), 500 kHz and 2.3 (C), 1 MHz and 3.3 (D), 2 MHz and 4.6 (E), and 4 MHz and 6/5 (F).

The lift-off vector 1, indicated by a straight line in the figure, is the locus of impedance values generated as the distance (lift-off) between the probe and the material is increased. The lift-off angle 2 is defined here as the angle whose tangent is the ratio of the change in the imaginary component to the change in the real component due to the material.

Each point on the normalized impedance curve 3 has associated with it a dimensionless reference number given by the ratio of the quantity, r, to the skin depth. This quantity, r, whose dimension is that of length, is related to the extent of the electromagnetic field associated with the probe. For the ferrite cup core probe this quantity is taken to be one third the outside diameter 20 of the core. Its relationship to the physical dimensions of the other ferrite core geometries is not defined herein. Turning now to FIG. 4, ferrite cup core probe 2 having a radius 30 and a diameter 20 can be visualized. The defect response vectors emanating from the designated reference points represent the magnitude of the change in impedance measured when the probe is in contact with defect-free material (base point) and the impedance, measured when the magnitude of the defect response is greatest.

If the reference point is close to the top of the curve, higher than point A, the lift-off line 2 will be very short. The magnitude of the defect vectors extending from this reference point will also be low. Not only must the frequency be appropriate to the thickness and resistivity of the material, the probe size must be appropriate to the skin depth. Assuming the skin depth is equal to the thickness of the material, the outside diameter of the ferrite cup core ideally must be at least 4.2 times the thickness. Since the effective radius of the ferrite cup core probe is ⅓ the outside diameter, the effective radius r of this probe, or any other probe, is 1.4 times the thickness to be inspected. Also the sensitivity to small defects decreases with increasing probe size, it is easier to detect small defects in thin material than in thick material.

The shape of a normalized impedance curve refers to its relative extent in the real and imaginary directions. The shape is described by the relationship between the reference number and lift-off angle. All normalized impedance curves generated by ferrite cup-core probes such as curve 3 in FIG. 1 were found to have a characteristic shape, termed herein a universal curve. The characteristic shape pertains when three conditions are met: the skin depth must be less than the thickness of the material; the inductance of the probe must have increased no more than 5% above its minimum value; and there must be no frequency dependent shielding effects.

The universal normalized impedance curve is highly significant. The relationship between the lift-off angle and reference number is a property of the probe core design and is insignificantly affected by lift-off and secondary probe design parameters such as the number and distribution of turns. The product of the probe means radius and the square root of the frequency can be treated as a normalizing factor. Regardless of the resistivity of the material, any particular point on the curve can be attained by the appropriate selection of the mean probe radius-frequency combination. This feature of the normalized impedance curve is the basis for the method of measuring defect depth disclosed herein.

The normalized impedance curve 3 and defect response vectors extending from each reference point A through F on FIG. 1 are typical of all the materials investigated where the skin depth was less than the material thickness. The carbon/carbon panel was 3.8 mm thick and contained three 12.7 mm diameter flat bottom holes (FBH). Their depths were approximately 10, 20, and 30% of the panel thickness.

Each reference point (A, B, ...) has an associated family of vectors. Each vector in the family corresponds to one of the three flat bottom holes. The larger the magnitude of the defect vector within each family the lesser the distance between the scan surface and the bottom of the flat bottom hole which breaks the back surface of the test material.

At each reference point on the curve (A, B, ...) the defect phase angle 4 depends on the quantity a/s; where a is the distance between the scan surface and the bottom of the flat bottom hole. Both the defect phase angle 4 and the quantity a/s were normalized with respect to the reference point on the curve. The normalized defect phase angle 5 is the difference between the defect phase angle 4 and the lift-off angle 2. The quantity a/s was multiplied by the reference number r/s. When the normalized defect angle was plotted against the square root of the quantity ar over s squared, the data for all the defect responses fell on a single curve described by the parabolic function $$\theta_n = C_1 + C_2(ar)^{\frac{1}{2}} + C_3 ar/s^2 \qquad \text{Equation 2}$$

where $\theta_n$ is the normalized defect angle 5.

The values of the coefficients for the ferrite cup core probe (r = ⅓ the outside diameter of the core) are $C_1 = -24.73$, $C_2 = 113.21$, and $C_3 = -17.492$.

As the probe is scanned across the surface some aspect of the impedance is monitored and a waveform is generated. The aspect of the impedance that is monitored can be its magnitude, its phase, either the real or imaginary component, or, typically, that component of the impedance that is normal to the lift-off vector.

While values of a can be calculated at each point in the waveform, these values are not measures of the depth of the damage at these points. Rather, it is the value of a, calculated at the point of maximum amplitude, that is the distance from the surface of the broken fiber damage that is nearest the surface.

Figure 2:
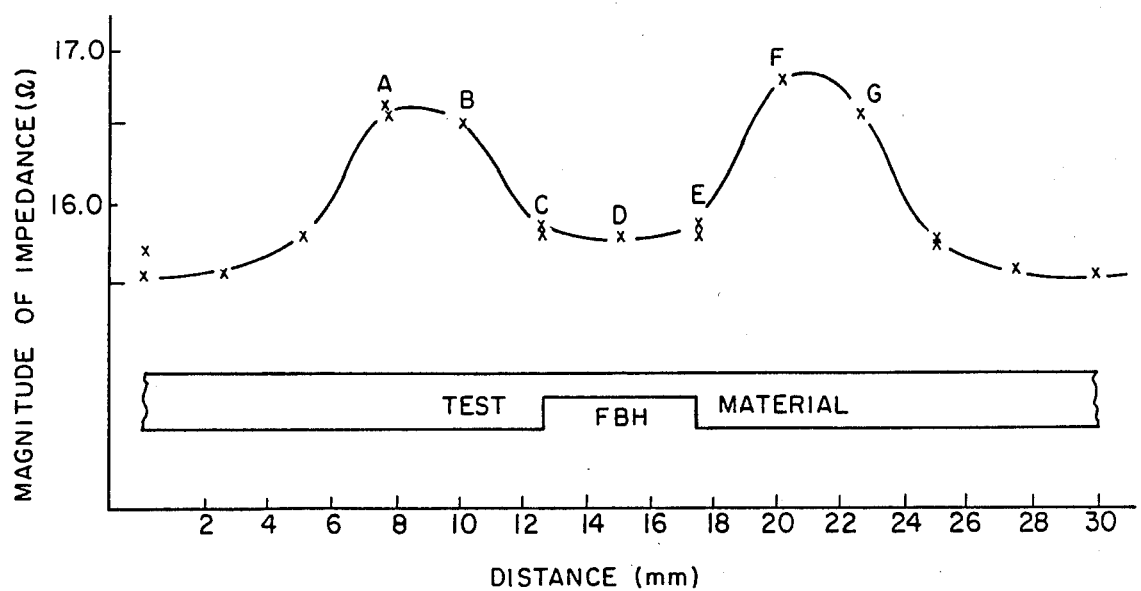
FIG. 2 is an impedance waveface generated during inspection of test material containing a flat bottom hole.

Turning now to FIG. 2, which graphs the change in impedance magnitude at 1 MHz as a 25.9 mm diameter probe was scanned across the surface of a graphite epoxy panel containing a back surface 6.4 mm diameter FBH. Values of a as calculated at points A through G are: 0.77, 0.771, 0.26, 0.40, 0.53, 0.56, and 0.46 mm, respectively. The actual value of a was 0.51 mm.

This waveform illustrates both the effect of the relative sizes of probe and defect on waveform shape and the effect of data selection point on the accuracy of the depth measurement. The double hump in the waveform of FIG. 2 is characteristic of the condition where the probe is much larger than the diameter of the defect. When the probe diameter and the defect diameter are similar in size there would result a single hump. Waveforms associated with cracks in thin metal plates differ only in that the horizontal scale is smaller, since both the probe diameter and the crack width are smaller. The most accurate estimate of the dimension a was made at point E (+2% error), while the estimate at F, the point of maximum amplitude, was high by 10% and the estimate at G was 10% low. Given the large error, on the order of 50%, which would result if any other points in the waveform were selected, it would seem fortuitous that even three points provided relatively accurate estimates. However, Applicants' experience has shown that the phase angle measured at the point of maximum impedance change provides an accuracy of plus or minus 10%, while measurements made in the dip result in widely varying estimates.

Figure 3:
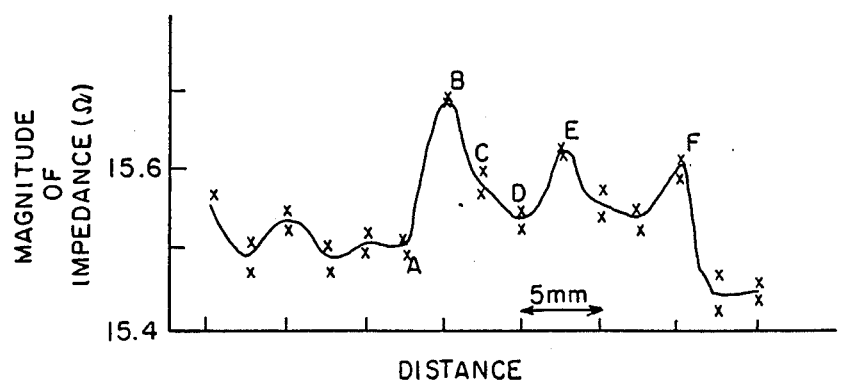
FIG. 3 is an impedance waveform generated during inspection of test material containing impact damage.

Directing attention to FIG. 3, an illustration is provided which graphs the magnitude of the impedance change at 4 MHz as a 14.1 mm diameter probe was scanned across the surface of an impact damaged graphite epoxy panel. Values of a calculated at points through E and F are: 0.18, 0.33, 0.43, 0.15, 0.44, 0.13 mm, respectively. The distance between the scan surface and the nearest delamination which also results from impact was estimated from an ultrasound A-scan to be 0.3 mm. It should be noted that the eddy current estimate at point B corresponds within 10% of the ultrasound measurement. Precise agreement is not expected since the two methods look at different aspects of the damage. Eddy current is sensitive to broken fibers while ultrasound is more responsive to delaminations.

2. Preferred method.

It intuitively follows from the above discussion that an effective method of determining the distance between the scan surface and the subsurface defect may be employed.

The method is based on the fact that for the ferrite cup core probe, and possibly for probes having ferrite cores with other geometries, secondary design characteristics such as number and distribution of windings have an insignificant effect on the relationship between the lift-off angle and the reference number. A probe design which exhibits this characteristic must be used. In addition to an appropriate probe core design, the size of the probe must be appropriate to the skin depth. Since the method addresses subsurface defects, the skin depth at the lowest frequency must be equal to or greater than the thickness, $T$, of the test material, thus, test material thickness determines the size of the probe. Optimally, the outside diameter of a ferrite cup core should be $7.56 \times T$ (or $r = 2.52 \times T$) and should be at least $4.2 \times T$.

The method may be implemented with a single frequency or a multifrequency approach. If a single frequency is used it should be such that the skin depth is equal to the thickness of the material. In a multifrequency approach this could be the lowest frequency. Each higher frequency can be twice the preceding lower frequency ($f_i = 2f_{i-1}$). The highest frequency need not be greater than that for which $r/s = 6$. The method of frequency selection is one of convenience and any method may be employed without departing from the scope of Applicants' invention.

Defect response phase angles must be normalized with respect to the lift-off angle. Data need not be normalized to calculate the defect phase angle, given by $$\theta_D = \tan^{-1}(X_d - X_b)/(R_b - d) \qquad \text{Equation 3}$$

In this relationship the air values of the real and imaginary components cancel out. However, the lift off angle, given by $$\theta_L = \tan^{-1}(1 - X_n)/R_n = (X_b - X_o)(R_b - R_oR) \qquad \text{Equation 4}$$

requires normalized impedance data. Data are first collected at the designated frequencies first with the probe in air then in contact with a region of the test material which is assumed to be free of defects. The values of the real and imaginary components of the impedance when the probe is in contact with good material represent the base data and are stored for future use in equation 3. The data are normalized using equation 1 and the lift-off angle is calculated (equation 4) and stored for future use. In the case of some CFRC, there may be localized variations in fiber density causing localized variations in resistivity. To help insure that the base data is representative of the material near the defect, it may be necessary to collect new base data near the point where a defect is detected in a CFRC.

The probe is scanned, either manually or via a computer controlled scanning device, over regions of the test material suspected of containing defects. Any scanning pattern including a raster scan may be employed. Some aspect of the probe impedance is monitored, preferably that component of the impedance which is normal to the lift-off vector. Several frequencies may be monitored, or, as in the preferred embodiment, only one. When the magnitude of the change in this monitored quantity exceeds some predetermined threshold, the probe is moved around to identify the point on the surface where the change is maximum. At this location, real and imaginary components of the impedance are collected at each of the designated frequencies. The defect phase angle (equation 3) associated with each frequency is calculated and normalized with respect to the appropriate stored lift-off angle, or $$\theta_n = \theta_D - \theta_L \qquad \text{Equation 5}$$

where $\theta_n$ is the normalized defect phase angle. $\theta_n$ is substituted in equation 2 along with the appropriate skin depth and probe radius $r$. Equation 2 is solved at each frequency for $a$, the distance between the scanned surface and the subsurface defect.

Ideally, all the calculated values of a would be identical. However, given the inherent noise in any experimental measurement, there is usually some scatter in the values. Any values which appear to be very different than the others can be ignored and the rest averaged to give an estimate of a.

Modifications and variations of the present invention are possible in light of the above teachings and within the purview of the appended claims without departing from the spirit and scope of the invention.

What we claim:

1. A method for estimating the distance (flaw depth) between the scanned surface and a subsurface flaw of unknown geometry from the effect of the flaw on the impedance of an eddy current probe consisting of the following steps:
   (a) providing an electrically conducting material to be tested; then
   (b) selecting a ferrite probe whose diameter is at least 4.2 times the thickness of said material over which inspection is desired; then
   (c) connecting the probe at said step (b) to an impedance measuring device; then
   (d) selecting on the impedance measuring device of said step (c) a range of frequencies such that at the lowest frequency selected the skin depth is equal to or greater than the thickness of the material provided at said step (a); then
   (e) measuring over frequency range at said step (d) the real ($R_o$) and imaginary ($X_o$) components of the probe impedance when the probe is "in air", far removed from any conductor; then
   (f) storing the data obtained in step (e); then
   (g) measuring, over the frequency range of said step (d), the real ($R_b$) and imaginary ($X_b$) components of the impedance of the probe of said step (b) when it is in contact with the test material at a point known to be free of defects; then
   (h) storing the data measured in step (g); then
   (i) calculating at each frequency, the lift-off angle, $\theta_L$, given by $$\theta_L = \tan^{-1}(X_o - X_b)/(R_b - R_o);$$

then
   (j) storing these data; then
   (k) scanning the probe selected in step (b) over the test material provided at said step (a) while monitoring one aspect of probe impedance and identifying the region where there is a distinct change in the monitored quantity; then
   (l) locating in the region identified in said step (k) the point where the magnitude of the monitored change is greatest; then
   (m) measuring, over the range of frequencies of said step (d), the real ($R_d$) and imaginary ($X_d$) components of the probe impedance at the point located in said step (l); then
   (n) calculating the normalized defect phase angle $\theta_n$, at each frequency measured in said step (m); then
   (o) substituting, at each frequency measured in said step (m), the normalized defect phase angle, $\theta_n$, calculated at said step (m), the skin depth, s, into the relationship $$\theta_n = C_1 + C_2(ar)^{\frac{1}{2}}/s + C_3 ar/s^2$$

where a is the depth of the subsurface defect and r is the mean radius of the probe selected in said step (b), and the coefficients, $C_1$, $C_2$, and $C_3$, have been empirically determined for the probe selected at said step (b), using flat bottom synthetic defects of known depth, and solving for a at each frequency; then
   (p) averaging those values from said step (o) which are randomly distributed about a mean.

2. A method according to claim 1 wherein the impedance measuring device of said step (c) is an eddy current circuit capable of generating frequencies between 10 KHz and 10 MHz.

3. A method according to claim 1 wherein the impedance measuring device of said step (c) is an impedance analyzer.

4. A method according to claim 1 wherein said step (d) is performed by selecting a range of frequencies such that at the lowest frequency the skin depth, s, is greater than or equal to the thickness of the test material at said step (a) and the highest is such that the ratio of the effective radius of the probe at said step (b) to the skin depth r/s is approximately 6.

5. A method according to claim 2 wherein said step (d) is performed by selecting a range of frequencies such that at the lowest frequency the skin depth, s, is greater than or equal to the thickness of the test material at said step (a) and the highest is such that the ratio of the effective radius of the probe at said step (b) to the skin depth r/s is approximately 6.

6. A method according to claim 3 wherein said step (d) is performed by selecting a range of frequencies such that at the lowest frequency the skin depth, s, is greater than or equal to the thickness of the test material at said step (a) and the highest is such that the ratio of the effective radius of the probe at said step (b) to the skin depth r/s is approximately 6.

7. A method for estimating the distance (defect depth) between the scanned surface and a subsurface defect of unknown geometry from the effect of the defect on the impedance of an eddy current probe consisting of the following steps:
   (a) providing an electrically conducting material to be tested; then
   (b) selecting as eddy current ferrite cup core probe whose diameter is at least 4.2 times the thickness of said material provided at step (a) over which inspection is desired; then
   (c) connecting the probe at said step (b) to an impedance measuring device; then
   (d) selecting on the impedance measuring device of said step (c) a range of frequencies such that at the lowest frequency selected the skin depth is equal to or greater than the thickness of the material provided at said step (a); then
   (e) measuring over frequency range at said step (d) the real ($R_o$) and imaginary ($X_o$) components of the probe impedance when the probe in "in air", far removed from any conductor; and
   (f) storing the data obtained in step (e); then
   (g) measuring, over the frequency range of said step (d), the real ($R_b$) and imaginary ($X_b$) components of the impedance of the probe of said step (b) when it is in contact with the test material at a point known to be free of flaws; and
   (h) storing the data measured in step (g); then
   (i) calculating at each frequency, the lift-off angle, $\theta_L$, given by $\theta_L = \tan^{-1}(X_o - X_b)/(R_b - R_o);$ then (j) storing these data; then (k) scanning the probe selected in step (b) over the test material provided at said step (a) while monitoring one aspect of probe impedance and identifying the region where there is a distinct change in the monitored quantity; then (l) locating in the region identified in said step (k) the point where the magnitude of the monitored change is greatest; then (m) measuring, over the range of frequencies of said step (d), the real ($R_d$) and imaginary ($X_d$) components of the probe impedance at the point located in said step (l); then (n) calculating the normalized flaw phase angle $\theta_n$, at each frequency measured in said step (m); then (o) substituting, at each frequency measured in said step (m), the normalized flaw phase angle, $\theta_n$, calculated at said step (m), the skin depth, s, into the relationship $$\theta_n = C_1 + C_2(ar)^{\frac{1}{2}}/s + C_3 ar/s^2$$

where a is the depth of the subsurface flaw and r is the mean radius of the probe selected in said step (b), and the coefficients, $C_1$, $C_2$ and $C_3$, are $-24.73$, $113.21$ and $-17.492$ respectively and solving for a at each frequency; then (p) averaging those values from said step (o) which are randomly distributed about a mean.

8. The method of claim 7 wherein the value of r in step (o) is at least 1.5 times the thickness of the test material.

9. The method of claim 7 wherein the value of r in step (o) is approximately 2.5 times the thickness of the test material.

10. The method of claim 1 wherein the range of frequencies chosen in step (d) are such that each frequency is twice that of the preceding lower frequency ($f_i = 2f_{i-1}$).

11. The method of claim 7 wherein the range of frequencies chosen in step (d) are such that each frequency is twice that of the preceding lower frequency ($f_i = 2f_{i-1}$).

12. A method for estimating the distance (defect depth) between the scanned surface and a subsurface defect of unknown geometry from the effect of the defect on the impedance of an eddy current probe consisting of the following steps:

(a) providing an electrically conducting material to be tested; then (b) selecting a ferrite probe which has a diameter at least 4.2 times the thickness of said material over which inspection is desired; then (c) connecting the probe at said step (b) to an impedance measuring device; then (d) selecting a single frequency on the impedance measuring device such that tan O falls between 0.8 and 6 inclusively; then (e) measuring the real ($R_o$) and imaginary ($X_o$) components of the probe impedance in air; then (f) storing the data obtained in step (e); then (g) measuring, over the frequency range of said step (d), the real ($R_b$) and imaginary ($X_b$) components of the impedance of the probe of said step (b) when it is in contact with the test material at a point known to be free of flaws; then (h) storing the data measured in step (g); then (i) calculating the lift-off, $\theta_L$, for the frequency selected at step (d), given by $$\theta_L = \tan^{-1}(X_o - X_b)/(R_b - R_o);$$

then (j) storing these data; then (k) scanning the probe selected in step (b) over the test material provided at said step (a) while monitoring one aspect of probe impedance and identifying the region where there is a distinct change in the monitored quantity; then (l) varying the probe around the point located in said step (k) to identify the location where the magnitude of the monitored change is greatest; then (m) measuring the real ($R_o$) and imaginary ($X_o$) components of the probe impedance at the point located in said step (l)

(n) calculating the normalized defect phase angle ($\theta_n$), at the frequency measured in said step (m); then (o) substituting, at each frequency measured in said step (m), the normalized flaw phase angle, $\theta_n$, calculated at said step (m), the skin depth, s, into the relationship $$\theta_n = C_1 + C_2(ar)^{\frac{1}{2}} s + C_3 ar/s^2$$

where a is the depth of the subsurface defect and r, is the mean radius of the probe selected in said step (b), and the coefficients, $C_1$, $C_2$, and $C_3$, have been empirically determined for the probe selected at said step (b), using flat bottom synthetic defects of known depth, and solving for a.

13. A method according to claim 1 wherein the aspect of probe impedance monitored in step (k) is the magnitude of the impedance monitored at a single frequency.

14. A method according to claim 1 wherein the aspect of probe impedance monitored in step (k) is the magnitude of the impedance monitored at a plurality of frequencies as selected in step (d).

15. A method according to claim 7 wherein the aspect of probe impedance monitored in step (k) is the magnitude of the impedance monitored at a single frequency.

16. A method according to claim 12 wherein the aspect of probe impedance monitored in step (k) is the magnitude of the impedance.

17. A method according to claim 7 wherein the aspect of probe impedance monitored in step (k) is the magnitude of the impedance monitored at a plurality of frequencies as selected in step (d).

18. A method according to claim 1 wherein the aspect of probe impedance monitored in step (k) is the phase of the impedance monitored at a single frequency.

19. A method according to claim 1 wherein the aspect of probe impedance monitored in step (k) is the phase of the impedance monitored at a plurality of frequencies as selected in step (d).

20. A method according to claim 7 wherein the aspect of probe impedance monitored in step (k) is the phase of the impedance monitored at a single frequency.

21. A method according to claim 12 wherein the aspect of probe impedance monitored in step (k) is the phase of the impedance.

22. A method according to claim 7 wherein the aspect of probe impedance monitored in step (k) is the phase of the impedance monitored at a plurality of frequencies as selected in step (d).

23. A method according to claim 1 wherein the aspect of probe impedance monitored in step (k) is the real component of the impedance monitored at a single frequency.

24. A method according to claim 1 wherein the aspect of probe impedance monitored at step (k) is the real component of the impedance monitored at a plurality of frequencies as selected in step (d).

25. A method according to claim 7 wherein the aspect of probe impedance monitored in step (k) is the real component of the impedance monitored at a single frequency.

26. A method according to claim 12 wherein the aspect of probe impedance monitored in step (k) is the real component of the impedance.

27. A method according to claim 7 wherein the aspect of probe impedance monitored at step (k) is the real component of the impedance monitored at a plurality of frequencies as selected in step (d).

28. A method according to claim 1 wherein the aspect of probe impedance monitored in step (k) is the imaginary component of the impedance monitored at a single frequency.

29. A method according to claim 1 wherein the aspect of probe impedance monitored at step (k) is the imaginary component of the impedance monitored at a plurality of frequencies as selected in step (d).

30. A method according to claim 7 wherein the aspect of probe impedance monitored in step (k) is the imaginary component of the impedance monitored at a single frequency.

31. A method according to claim 12 wherein the aspect of probe impedance monitored in step (k) is the imaginary component of the impedance.

32. A method according to claim 7 wherein the aspect of probe impedance monitored at step (k) is the imaginary component of the impedance monitored at a plurality of frequencies as selected in step (d).

33. A method according to claim 1 wherein the aspect of probe impedance monitored in step (k) is that component of the impedance that is normal to the lift of vector monitored at a single frequency.

34. A method according to claim 1 wherein the aspect of probe impedance monitored at step (k) is that component of impedance that is normal to the lift-off vector monitored at a plurality of frequencies as selected in step (d).

35. A method according to claim 7 wherein the aspect of probe impedance monitored in step (k) is that component of the impedance that is normal to the lift of vector monitored at a single frequency.

36. A method according to claim 12 wherein the aspect of probe impedance monitored at step (k) is that component of impedance that is normal to the lift-off vector.

37. A method according to claim 7 wherein the aspect of probe impedance monitored at step (k) is that component of impedance that is normal to the lift-off vector monitored at a plurality of frequencies as selected in step (d).

38. The method of claim 1 wherein said step (p) is accomplished by selecting the value of a associated with the highest frequency that is not out of line with the others.

39. The method according to claim 7 wherein said step (p) is accomplished by selecting the value of a associated with the highest frequency that is not out of line with the others.

40. The method of claim 1 wherein said step (p) is accomplished by averaging those calculated values of a excluding any values out of line with the others.

41. The method according to claim 7 wherein said step (p) is accomplished by averaging those calculated values of a excluding any values out of line with the others.

42. The method of claim 12 wherein the probe selected in said step (b) is a ferrite cup core.

43. The method of claim 1 wherein the scanning of the probe in said step (k) is automated.

44. The method of claim 43 wherein the scanning of the probe in said step (k) is an automated raster scan.

45. The method of claim 1 wherein said steps (k), (l), (m), (n), (o) and (p) are performed automatically without operator intervention.

* * * * *